United States Patent [19]

Cheng et al.

[11] Patent Number: 4,514,620

[45] Date of Patent: Apr. 30, 1985

[54] CONDUCTIVE POLYMERS EXHIBITING PTC CHARACTERISTICS

[75] Inventors: Tai C. Cheng, Mountain View; Bruce A. McKinley, Fremont, both of Calif.

[73] Assignee: Raychem Corporation, Menlo Park, Calif.

[21] Appl. No.: 535,449

[22] Filed: Sep. 22, 1983

[51] Int. Cl.³ ............................................. H05B 3/10
[52] U.S. Cl. .................................... 219/553; 219/505; 219/528; 219/549; 252/511; 264/105; 338/22 R; 338/22 SD
[58] Field of Search ............... 219/345, 505, 528, 548, 219/549, 552, 553; 174/92, 102 R, 102 SC, DIG. 8; 332/22 R, 22 SD, 214; 252/510, 511, 512; 264/105, 346; 428/214; 29/611

[56] References Cited

U.S. PATENT DOCUMENTS

| | | | |
|---|---|---|---|
| 3,621,192 | 11/1971 | Pohler | 219/217 |
| 3,732,338 | 5/1973 | Theisen et al. | 260/897 |
| 3,751,620 | 8/1973 | Yuasa | 219/211 |
| 3,757,088 | 9/1973 | Osborn | 219/553 |
| 3,768,156 | 10/1973 | Caird et al. | 29/611 |
| 3,808,403 | 4/1974 | Kanaya et al. | 219/528 |
| 3,858,144 | 12/1974 | Bedard et al. | 338/22 |
| 3,900,654 | 8/1975 | Stinger | 428/214 |
| 4,177,446 | 12/1979 | Diaz | 338/212 |
| 4,246,468 | 1/1981 | Horsma | 219/553 |
| 4,250,397 | 2/1971 | Gray et al. | 219/345 |
| 4,250,398 | 2/1981 | Ellis et al. | 219/345 |
| 4,265,789 | 5/1981 | Christopherson et al. | 428/367 |
| 4,271,350 | 6/1981 | Crowley | 219/549 |
| 4,304,987 | 12/1981 | van Konynenburg | 219/553 |
| 4,309,596 | 1/1982 | Crowley | 219/549 |
| 4,309,597 | 1/1982 | Crowley | 219/549 |
| 4,330,704 | 5/1982 | Jensen | 219/553 |
| 4,348,584 | 9/1982 | Gale et al. | 219/549 |
| 4,400,614 | 8/1983 | Sopory | 219/528 |
| 4,429,216 | 1/1984 | Brigham | 219/528 |

FOREIGN PATENT DOCUMENTS 1,640,842 9/1970 Fed. Rep. of Germany .
1,503,387 3/1978 United Kingdom .

OTHER PUBLICATIONS

The Stereo Rubbers, by Wm. M. Saltman, pp. 285–364.
Elastomerics, by Adolf Draxler, pp. 16–20, Feb. 1983.
Kautschuk-Lexikon (Heinisch) pp. 432–433 European Search Report.

Primary Examiner—Volodymyr Y. Mayewsky
Attorney, Agent, or Firm—Timothy H. P. Richardson; Herbert G. Burkard

[57] ABSTRACT

Conductive polymer compositions which exhibit PTC behavior and comprise carbon black (or other particulate conductive filler) dispersed in a cross-linked polymer component comprising a cycloolefin polymer having a crystallinity of at least 5% and a melting point in the range 0° to 80° C. These compositions are particularly useful in the form of heaters which self regulate at a temperature in the range of 0° to 70° C. Such heaters are particularly useful for freeze protection and for heating human and other animal bodies.

25 Claims, No Drawings

CONDUCTIVE POLYMERS EXHIBITING PTC CHARACTERISTICS

BACKGROUND OF THE INVENTION

1. Field of the Invention

This invention relates to conductive polymer compositions which exhibit PTC behavior and to devices comprising them.

2. Introduction to the Invention

It is known that polymers, including crystalline polymers, can be made electrically conductive by dispersing therein suitable amounts of carbon black or another finely divided conductive filler. Some conductive polymers exhibit what is known as PTC (positive temperature coefficient) behavior. The terms "composition exhibiting PTC behavior" and "PTC composition" are used in this specification to denote a composition which has an $R_{14}$ value of at least 2.5 and an $R_{100}$ value of at least 10, and preferably has an $R_{30}$ value of at least 6, where $R_{14}$ is the ratio of the resistivities at the end and the beginning of a 14° C. range, $R_{100}$ is the ratio of the resistivities at the end and the beginning of a 100° range, and $R_{30}$ is the ratio of the resistivities at the end and the beginning of a 30° C. range. A plot of the log of the resistance of a PTC element (i.e. an element composed of a PTC composition) against temperature will often show a sharp change in slope over a part of the temperature range in which the composition has an $R_{100}$ value of at least 10. The term "switching temperature" (usually abreviated to $T_s$) is used herein to denote the temperature at the intersection point of extensions of the substantially straight portions of such a plot which lie either side of the portion showing the sharp change in slope.

Electrical devices comprising conductive polymer elements, in particular heaters, circuit control devices, and sensors, have been described in prior publications and in co-pending, commonly assigned, patent applications. Reference may be made for example to U.S. Pat. Nos. 2,952,761, 2,978,665, 3,243,753, 3,351,882, 3,571,777, 3,757,086, 3,793,716, 3,823,217, 3,858,144, 3,861,029, 4,017,715, 4,072,848, 4,085,286, 4,117,312, 4,177,376, 4,177,446, 4,188,276, 4,237,441, 4,242,573, 4,246,468, 4,250,400, 4,255,698, 4,271,350, 4,272,471, 4,304,987, 4,309,596, 4,309,597, 4,314,230, 4,315,237, 4,317,027, 4,318,881, 4,330,704, 4,334,351 and 4,388,607; J. Applied Polymer Science 19, 813–815 (1975), Klason and Kubat; Polymer Engineering and Science 18, 649–653 (1978), Narkis et al; and commonly assigned U.S. Ser. Nos. 601,424 (Moyer), now abandoned, published as German OLS No. 2,634,999; 750,149 (Kamath et al.), now abandoned, published as German OLS No. 2,755,077; 732,792 (Van Konynenburg et al), now abandoned, published as German OLS No. 2,746,602; 798,154 (Horsma et al), now abandoned, published as German OLS No. 2,821,799; 134,354 (Lutz); 141,984 (Gotcher et al.), published as European Application No. 38718; 141,987 (Middleman et al.), published as European Application No. 38715, 141,988 (Fouts et al.), also published as European Application No. 38718, 141,989 (Evans), published as European Application No. 38713, 141,991 (Fouts et al.), published as European Application No. 38714, 142,053 (Middleman et al.), now U.S. Pat. No. 4,352,083 254,352 (Taylor) now U.S. Pat. No. 4,426,633, 273,525 now U.S. Pat. No. 398,084 (Walty), 300,709 (van Konynenburg et al.), 349,505 (McTavish et al.), 369,309 (Midgley et al.), 380,400 (Kamath), 403,203 (Stewart et al.) 418,354 (Gurevich), 423,589 (Van Konynenburg et al.), 483,633 (Wasley) and 509,897 (Masia et al.). The disclosure of each of the patents, publications and applications referred to above is incorporated herein by reference.

SUMMARY OF THE INVENTION

We have now discovered that conductive polymer compositions having very valuable properties can be obtained by dispersing carbon black (or another particulate conductive filler) in a polymeric component which comprises a substantial proportion of a crystalline cycloolefin polymer. In particular, we have found that such compositions exhibit PTC behavior with a $T_s$ which corresponds to (and generally is 5° to 100° C., eg. 10° to 40° C. below) the crystalline melting point of the cycloolefin polymer, which is generally in the range of 0° to 80° C. Especially when the polymer has a melting point below ambient temperature and/or when it is important that the composition has good physical properties, especially flexibility, it is desirable or essential that the composition is cross-linked.

In one aspect, the invention provides an electrical device, especially a heater, which comprises (1) a PTC element which is composed of a conductive polymer composition which exhibits PTC behavior and which comprises (a) a cross-linked polymer component which comprises at least 15%, generally at least 20% by weight of repeating units derived from a cycloolefin, which has a crystallinity of at least 10% and which has a crystalline melting point in the range of 0° to 70° C., and (b) a particulate conductive filler which is dispersed in said polymer; and (2) at least two electrodes which can be connected to a source of electrical power to cause current to flow through the PTC element.

In another aspect, the invention includes conductive polymer compositions as defined above.

DETAILED DESCRIPTION OF THE INVENTION

The PTC compositions used in this invention comprise a cross-linked polymeric component which (a) comprises at least 15%, generally at least 20%, preferably at least 50%, especially 50 to 90%, by weight of units derived from a substituted or unsubstituted cycloolefin, preferably a cycloolefin containing 5 to 12 carbon atoms in the ring;

(b) has a crystallinity (crystallinities given in this specification are measured by differential scanning calorimetry (DSC) using high density polyethylene as the standard) of at least 5%, preferably at least 8% (with values of 8–15% being generally preferred for heaters and values above 15% being generally preferred for circuit protection devices); and (c) has a crystalline melting point of 0° to 80° C., preferably 25° to 70° C.

The cycloolefin units can be derived from a single cycloolefin or from a mixture of two or more cycloolefins. Polymerization of cycloolefins generally results in repeating units which are ethylenically unsaturated, and cycloolefin polymers are, therefore, often referred to as polyalkenamers. The cycloolefin units are preferably present as a polymer in which substantially all the repeating units are derived from one or more cycloolefins; however, they can also be present as part of a block or random copolymer which also contains units derived from one or more copolymerisable monomers, eg. an acyclic olefin. The cycloolefin can be a substituted or unsubstituted monocyclic or multicyclic (including dicyclic) monoolefin or multiolefin (including diolefin), eg. cyclopentene, cycloheptene, cyclooctene, cyclododecene, 1,5-cyclooctadiene, 1,5,9-cyclododecadiene,-norbornene, norbornadiene, ethylidene norbornene and dicyclopentadiene. The preparation and properties of cycloolefin polymers is described in "The Stereo Rubbers", edited by Saltman and published by John Wiley and Sons (1977), pages 285 to 364, the disclosure of which is incorporated herein by reference. These polymers are generally characterized by a low melting point (usually in the range 0° to 80° C.) which can to some extent be controlled by regulating the cis/trans ratio (and hence the crystallinity) of the polymer; the trans content of the polymer is generally at least 60%, eg. 60 to 90%. The polymer retains cyclic rings in its structure, and these rings may be interlocked, eg. as in the catenanes or nectinodanes. Particularly good results have been obtained in the present invention using polyoctenamer with a trans content of 60 to 90% (melting point about 30° C. to about 70° C.).

The polymer component can contain units derived from one or more monomers which are not cycloolefins. Such units can be present as part of a copolymer with a cycloolefin, but are preferably present in a second polymer which is free from units derived from a cycloolefin. The second polymer may be crystalline, for example a polymer of one or more acyclic substituted or unsubstituted olefins, a polyester or a polylactone; if present, such a polymer can be present in amount, for example, of 10 to 50% by weight of the total polymer component. Alternatively, the second polymer can be amorphous, preferably an elastomer, eg. polybutadiene or an ethylene/propylene/diene polymer (EPDM); such a polymer can be present in amount, for example, of 5 to 15% by weight of the total polymer component, and frequently serves to improve the melt processability of the composition, and/or its physical properties after processing.

The particulate conductive filler preferably consists essentially of carbon black, particularly one which has a particle size (D) of 20 to 150 millimicrons and a surface area (S) in $m^2/g$ such that the ratio S/D is not more than 10. However, the invention includes the use of other conductive fillers in place of all or part of the carbon black. The amount of conductive filler should be such that the composition has the desired resistivity, usually 1 to $5 \times 10^5$ ohm·cm, preferably $10^3$ to $10^5$ ohm·cm for heaters powered by line voltages, eg. of 120 or 240 V AC, and preferably 10 to 1000 ohm·cm for heaters powered by battery voltages, eg. 4 to 48 volts.

The conductive polymer composition preferably also contains an antioxidant, preferably in amount 0.5 to 4%, particularly 1 to 3%, by volume, based on the volume of the polymeric component. The melting point of the antioxidant is preferably below the temperature at which the polymers processed, eg. below 100° C., preferably 40° to 100° C. Particularly good results have been obtained using antioxidants which contain a hindered phenol group, preferably a 1,3-di-t-butyl-2-hydroxy phenyl group; which preferably have a molecular weight greater than 400, particularly greater than 600; and which may or may not contain a thio, ester, amino or other functional group; for example the antioxidants of this type sold by Ciba Geigy under the trade name Irganox. The presence of the antioxidant is important in preventing degradation of the polymer during processing and in ensuring that there is not an excessive change in the resistivity of the composition when it is subjected to temperatures in the operating range of the device, eg. 0° to 70° C.

The conductive polymer composition can also contain conventional ingredients such as non-conductive fillers, processing aids, pigments and fire retardants, and, when the composition is to be cross-linked chemically, suitable cross-linking agents.

The conductive polymer composition is preferably shaped by melt-extrusion, molding or another melt-shaping operation. It is important to avoid excessive mixing time or intensity, which can cause the product to have too high a resistivity. It is also possible to process the composition in the form of a solution, eg. by casting a solution of the conductive polymer which is then allowed to dry. If desired, the polymer can be lightly cross-linked before it is shaped, eg. by irradiation to a dose of 1 to 6 Mrad.

After the composition has been shaped, it should be cross-linked. Cross-linking is preferably effected by radiation, eg. by an electron beam, to a dosage which adequately cross-links but does not deleteriously degrade the polymeric component, eg. in the range 2 to 100 Mrad, preferably 3 to 30 Mrad, eg. 5 to 15 Mrad. Alternatively, cross-linking can be effected with the aid of a chemical cross-linking agent, eg. a peroxide such as dicumyl peroxide or sulfur. In the absence of such cross-linking, the PTC element may become very brittle, thus severely limiting the practical utility of the device. If the composition is not cross-linked within a relatively short time after processing eg. within a week or two, it becomes progressively more brittle. However, if the shaped composition is reheated, its flexibility can be restored. The temperature increase required is not large and can be provided in a suitable cross-linking step, eg. by using a suitably high rate of radiation, and the cross-linking will preserve the flexibility permanently.

The PTC element and the electrodes can be of any shape and dimension which results in a useful device, for example as disclosed in the publications referenced above, especially a heater or a circuit protection device. The electrodes can be in physical contact with the PTC element or physically separated therefrom by a conductive layer, eg. of a conductive polymer composition exhibiting ZTC behavior, preferably a ZTC conductive polymer based on a substantially amorphous polycycloolefin.

The present invention provides greatly improved heaters which will self-regulate at a temperature in the range of $-20°$ to 70° C. Furthermore, by selecting a suitable cycloolefin and if necessary adjusting the cis/trans ratio of the polymer, the $T_s$ of the heater (and hence the substrate temperature which it will maintain) can be adjusted according to the particular end result desired. For example, for freeze protection, a heater having a $T_s$ of 0° to 40° C., eg. 5° to 25° C., is particularly useful. For heating the human body, a $T_s$ of 20° to 50° C. is desirable, since the surface temperature of the heater should be less than about 45° C. to ensure that the skin is not thermally injured. Furthermore, the conductive polymer compositions used in the heaters (and other devices) of the invention not only have good resistivity/temperature characteristics, but also can be processed by conventional techniques, can be cross-linked to give satisfactory mechanical properties, in particular flexibility and toughness, and have good resistance stability. Earlier attempts to make such heaters have not been wholly successful. For example, PTC compositions based on cis-1,4-polybutadiene do not increase sufficiently in resistivity when heated; poly-ε-caprolactone has a melting point (about 65° C.) which is too high for many purposes and has poor physical properties, especially above the melting point; and compositions comprising low-melting waxes are not resistance-stable and have poor physical properties.

The invention is illustrated by the following Examples, which are summarized in Tables 1 and 2 below. In each of the Examples, the ingredients and amounts thereof indicated in the Tables were used (note that the amounts are in parts by volume in Table 1 and in parts by weight in Table 2).

In Examples 1 to 8, the ingredients were melt-blended in a Brabender, and the blend was compression molded into a plaque. The plaque was then irradiated to the dosage shown in the Table. Silver paint electrodes were placed on the plaque, and the change in resistivity of the composition with temperature was determined. Each of the compositions exhibited a good PTC effect.

In each of Examples 9, 10 and 11, the ingredients were fed at metered rates to the barrel of twin screw extruder fitted with a cross-head die, and the resulting mixture was melt extruded around a pair of parallel wire electrodes to form a strip heater of conventional cross-section, which was then cross-linked by radiation to the dose shown.

In each of Examples 12, 13, 14 and 16, the ingredients were melt blended on a Banbury, and the blend was diced and melt extruded around a pair of parallel wire electrodes to form a strip heater of conventional cross-section. which was then cross-linked by radiation to the dose shown.

In Example 15, the ingredients were dry-blended and then dumped into the hopper of a single screw extruder through which the mixture was melt-extruded around a pair of parallel wire electrodes to form a strip heater of conventional cross-section. which was then cross-linked by radiation to the dose shown.

The various ingredients given in the Tables are further identified below.

Vestenamer 8012 is sold by Hüls and is a polymer of cyclooctene having a trans content of about 80%, a crystalline melting point of about 55° C., and a crystallinity of about 11% (corresponding to a crystallinity of about 32% measured by DSC by reference to 100% crystalline polycyclooctene). In Examples 9 and 10, as indicated by the asterisk, the polymer was pre-irradiated to a dose of 5 Mrad.

Petrothene NA-344 is a low density polyethylene sold by ICI.

DYNH-1 is a low density polyethylene sold by Union Carbide.

DPD-6169 is an ethylene/ethyl acrylate copolymer sold by Union Carbide.

Vistalon 1721 is an ethylene/propylene rubber sold by Exxon.

TPR-5490 is a thermoplastic rubber sold by Reichhold Chemical.

DHDA-7704 is sold by Union Carbide and is a dispersion of a carbon black (about 38% by weight) in an ethylene/ethyl acrylate copolymer.

Statex G is a carbon black sold by Columbian Chemicals.

XC-72 is a carbon black sold by Cabot as Vulcan XC-72.

Black Pearls 2000 is a carbon black sold by Cabot.

Irganox 1035 is a hindered phenol antioxidant sold by Ciba Geigy.

TABLE I

| | EXAMPLE NO. | | | | | | | | | | |
|---|---|---|---|---|---|---|---|---|---|---|---|
| | 1 | 2 | 3 | 4 | 5 | 6 | 7 | 8 | 9 | 10 | 11 |
| Vestenamer 8012 | 99 | 79 | 66 | 79 | 66 | 74 | 66 | 89 | 99* | 84* | 84 |
| DPD 6169 | — | — | — | 20 | 33 | — | — | — | — | — | — |
| DYNH-1 | — | 20 | 33 | — | — | — | — | 10 | — | 15 | 15 |
| Vistalon 1721 | — | — | — | — | — | 25 | 33 | — | — | — | — |
| Statex G | 25 | 25 | 25 | 25 | 25 | 25 | 25 | 25 | 25 | 25 | 25 |
| Irganox 1035 | 1 | 1 | 1 | 1 | 1 | 1 | 1 | 1 | 1 | 1 | 1 |
| Dose (Mrad) | 10 | 10 | 10 | 10 | 10 | 10 | 10 | 10 | 10 | 10 | 10 |
| Log Resistivity (ohm · cm) at 20° C. | 2 | 3 | 2.5 | 2 | 2.5 | 3 | 3 | 3.5 | | | |

TABLE 2

| | EXAMPLE NO. | | | | |
|---|---|---|---|---|---|
| | 12 | 13 | 14 | 15 | 16 |
| Vestenamer | 83 | 69.5 | 21 | 43 | 30 |
| Petrothane NA-344 | — | 15 | — | — | 10 |
| TPR-5490 | — | — | 63 | — | — |
| DHDA 7704 | — | — | — | 56 | 58 |
| XC-72 | 16 | 14.5 | 12.4 | — | |
| Black Pearls 2000 | — | — | 2.6 | — | |
| Irganox 1035 | 1 | 1 | 1 | 1 | 2 |
| Mrad | 5 | 5 | 5 | 5 | 5 |

We claim:

1. An electrical device which comprises a
(1) a PTC element which is composed of a conductive polymer composition which exhibits PTC behavior and which comprises
   (a) a cross-linked polymer component which comprises at least 15% by weight of repeating units derived from a cycloolefin, which has a crystallinity of at least 5% and which has a crystalline melting point in the range of 0° to 80° C., and
   (b) a particulate conductive filler which is dispersed in said polymer; and
(2) at least two electrodes which can be connected to a source of electrical power to cause current to flow through the PTC element.

2. A device according to claim 1 wherein the polymer component comprises at least 50% by weight of a cycloolefin polymer in which at least 80% by weight of the repeating units are derived from at least one cycloolefin.

3. A device according to claim 2 wherein said cycloolefin is free from substituents.

4. A device according to claim 2 wherein the polymer component comprises a blend of 50 to 90% by weight of said cycloolefin polymer and 10 to 50% by weight of an acyclic olefin polymer.

5. A device according to claim 1 wherein the polymer component comprises a polymer of cyclooctenamer having a trans content of 60 to 90%.

6. A device according to claim 1 wherein the polymer component has been cross-linked by radiation.

7. A device according to claim 6 wherein the polymer component has been cross-linked by radiation to a dosage of 5 to 30 Mrad.

8. A device according to claim 1 wherein the polymer component has been cross-linked with the aid of a chemical cross-linking agent.

9. A device according to claim 1 which further comprises
(3) an antioxidant which is a hindered phenol.

10. A device according to claim 9 wherein the antioxidant contains a 1,3-di-t-butyl-2-hydroxy group.

11. A device according to claim 9 wherein the antioxidant has a molecular weight of at least 600.

12. A device according to claim 1 which further comprises
(3) an antioxidant which has a melting point of 40° to 100° C.

13. A device according to claim 1 wherein the particulate conductive filler consists essentially of carbon black.

14. A device according to claim 13 wherein the carbon black has a particle size (D) of 20 to 250 millimicrons and a surface area (S) such that the ratio S/D is not more than 10.

15. A device according to claim 1 wherein the PTC element has been prepared by melt-shaping and subsequently cross-linking a mixture of the polymer and the conductive filler.

16. A device according to claim 1 which is a strip heater comprising two elongate parallel electrodes which are embedded in an elongate PTC element.

17. A device according to claim 1 which is a sheet heater.

18. A conductive polymer composition which exhibits PTC behavior and which comprises
(a) a cross-linked polymer component which comprises at least 15% by weight of repeating units derived from a cycloolefin, which has a crystallinity of at least 5% and which has a crystalline melting point in the range of 0° to 80° C., and
(b) a particulate conductive filler which is dispersed in said polymer.

19. A composition according to claim 18 wherein the polymer is cyclooctenamer and the conductive filler is carbon black, and which further comprises an antioxidant which has a molecular weight of at least 600 and a melting point of 40° to 100° C.

20. A composition according to claim 18 wherein the polymer component comprises at least 50% by weight of a cycloolefin polymer in which at least 80% by weight of the repeating units are derived from at least one cycloolefin.

21. A composition according to claim 20 wherein the polymer component comprises a blend of 50 to 90% by weight of said cycloolefin polymer and 10 to 50% by weight of an acyclic olefin polymer.

22. A composition according to claim 18 wherein the polymer component has been cross-linked by radiation.

23. A composition according to claim 18 which further comprises an antioxidant which is a hindered phenol having a molecular weight of at least 600.

24. A composition according to claim 18 which further comprises an antioxidant which has a melting point of 40° to 100° C.

25. A composition according to claim 18 wherein the particulate conductive filler consists essentially of carbon black having a particle size (D) of 20 to 250 millimicrons and a surface area (S) such that the ratio S/D is not more than 10.

* * * * *